United States Patent
Jones et al.

(10) Patent No.: US 9,636,665 B2
(45) Date of Patent: May 2, 2017

(54) CATALYST COMPOSITIONS FOR CONVERTING SYNGAS TO PRODUCE HIGHER ALCOHOLS

(75) Inventors: Christopher W. Jones, Mableton, GA (US); Pradeep K. Agrawal, Atlanta, GA (US); Tien Thao Nguyen, Viet Hung (VN)

(73) Assignee: Georgia Tech Research Corporation, Atlanta, GA (US)

( * ) Notice: Subject to any disclaimer, the term of this patent is extended or adjusted under 35 U.S.C. 154(b) by 273 days.

(21) Appl. No.: 13/883,686

(22) PCT Filed: Dec. 1, 2011

(86) PCT No.: PCT/US2011/062760
§ 371 (c)(1),
(2), (4) Date: May 6, 2013

(87) PCT Pub. No.: WO2012/078437
PCT Pub. Date: Jun. 14, 2012

(65) Prior Publication Data
US 2013/0245328 A1    Sep. 19, 2013

Related U.S. Application Data

(60) Provisional application No. 61/419,941, filed on Dec. 6, 2010.

(51) Int. Cl.
| | | |
|---|---|---|
| *C07C 27/06* | (2006.01) | |
| *B01J 27/236* | (2006.01) | |
| *B01J 23/00* | (2006.01) | |
| *B01J 23/28* | (2006.01) | |
| *C07C 29/153* | (2006.01) | |

(52) U.S. Cl.
CPC ........... *B01J 27/236* (2013.01); *B01J 23/007* (2013.01); *B01J 23/28* (2013.01); *C07C 27/06* (2013.01); *C07C 29/153* (2013.01)

(58) Field of Classification Search
CPC .................................................... C07C 27/06
USPC .................. 518/713, 714; 502/206, 241, 211
See application file for complete search history.

(56) References Cited

U.S. PATENT DOCUMENTS

| | | |
|---|---|---|
| 3,787,332 A | 1/1974 | Sugier |
| 4,126,581 A | 11/1978 | Sugier et al. |
| 4,257,920 A | 3/1981 | Sugier et al. |
| 4,346,179 A | 8/1982 | Sugier et al. |
| 4,590,314 A | 5/1986 | Kinkade |
| 4,593,015 A | 6/1986 | Hardman et al. |
| 4,607,055 A | 8/1986 | Grazioso et al. |
| 4,609,678 A | 9/1986 | Hardman et al. |
| 4,661,525 A | 4/1987 | Grazioso et al. |
| 4,675,344 A | 6/1987 | Conway et al. |
| 4,725,625 A | 2/1988 | Simon |
| 4,749,724 A | 6/1988 | Quarderer et al. |
| 4,751,248 A | 6/1988 | Lin et al. |
| 4,752,622 A | 6/1988 | Stevens |
| 4,752,623 A | 6/1988 | Stevens et al. |
| 4,825,013 A | 4/1989 | Quarderer et al. |
| 4,883,533 A | 11/1989 | Kosin et al. |
| 5,627,295 A | 5/1997 | Sofianos et al. |
| 5,851,382 A | 12/1998 | Sudhakar |
| 6,927,048 B2 | 8/2005 | Verser et al. |
| 7,196,122 B2 | 3/2007 | Ryoo et al. |
| 7,314,960 B1 | 1/2008 | Lin et al. |
| 7,449,425 B2 | 11/2008 | Wang et al. |
| 7,569,318 B2 | 8/2009 | Michel et al. |
| 7,658,776 B1 | 2/2010 | Pearson |
| 7,682,812 B2 | 3/2010 | Verser et al. |
| 7,700,810 B2 | 4/2010 | Kourtakis et al. |
| 7,700,811 B2 | 4/2010 | Kourtakis et al. |
| 7,700,813 B2 | 4/2010 | Kourtakis et al. |
| 7,705,192 B2 | 4/2010 | Kourtakis et al. |
| 7,717,971 B2 | 5/2010 | Aasberg-Petersen et al. |
| 7,718,832 B1 | 5/2010 | Hurley et al. |
| 2007/0004588 A1 | 1/2007 | Wang et al. |
| 2010/0075837 A1 | 3/2010 | Meitzner et al. |
| 2010/0280287 A1 | 11/2010 | Kharas et al. |

FOREIGN PATENT DOCUMENTS

| | | |
|---|---|---|
| CN | 101020139 A | 8/2007 |
| EP | 0119609 A1 | 9/1984 |
| EP | 0149256 A2 | 7/1985 |
| EP | 0172431 | 2/1986 |
| WO | WO-2007/127479 A2 | 11/2007 |

OTHER PUBLICATIONS

Abdel-Rahman, International Journal of Energy Research, 1997, vol. 21, Issue 1, p. 31-40.
Bang-Quan, Atmospheric Environment, 2003, vol. 37, p. 4965-4971.
Bao, Topics in Catalysis, 2009, vol. 52, p. 789-794.
Bezemer, Chemical Communications, 2005, p. 731-733.
Cavani, Catalysis Today, 1991, vol. 11, Issue 2, p. 173-301.
Christensen, Applied Catalysis A: General, 2009, vol. 366, Issue 1, p. 29-43.
Cortes-Jacome, Catalysis Today, 2008, vol. 130, p. 56-62.
Danilov, Chemistry and Technology of Fuels and Oils, 2001, vol. 37, Issue 6, p. 444-455.
Fan, Catalysis Today, 2009, vol. 147, p. 86-93.
Fang, Catalysis Today, 2009, vol. 147, Issue 2, 133-138.
Forzatti, Catalysis Reviews: Science and Engineering, 1991, vol. 33, Issue 1&2, p. 109-168.
Gomez-Hortigu, Journal of the American Chemical Society, 2009, vol. 131, p. 16509-16524.
Haider, Journal of Catalysis, 2009, vol. 261, Issue 1, p. 9-16.
Herman, Catalysis Today, 2000, vol. 55, Issue 3, p. 233-245.
Iranmahboob, Applied Catalysis A: General, 2002, vol. 231, p. 99-108.

(Continued)

*Primary Examiner* — Elvis O Price
(74) *Attorney, Agent, or Firm* — Dinsmore & Shohl LLP

(57) ABSTRACT

Catalyst compositions for production of higher alcohols comprise a hydrotalcite or hydrotalcite-like support impregnated with molybdenum and an alkali metal. When the compositions are used to convert syngas, selectivity to higher (C2+) alcohols is increased in comparison to conversions accomplished over many other catalyst systems.

7 Claims, No Drawings

(56) References Cited

OTHER PUBLICATIONS

Iranmahboob, Applied Catalysis A: General, 2003, vol. 247, Issue 2, p. 207-218.
Jiao, Journal of Catalysis, 2008, vol. 260, 342-350.
Jun, Journal of the American Chemical Society, 2000, vol. 122, p. 10712-10719.
Juncheng, The Journal of Physical Chemistry C, 2007, vol. 111, p. 12038-12044.
Li, Fuel Processing Technology, 2007, 88, 125-127.
Li, Topics in Catalysis, 2005, vol. 32, Issue 3-4, p. 233-239.
Mallada, Applied Catalysis A: General, 2002, vol. 231, p. 109-116.
McDonald, Microporous and Mesoporous Materials, 2009, vol. 120, p. 263-266.
Morrill, Catal. Lett, 2012, vol. 142, p. 875-881.
Nunan, Journal of Catalysis, 1989, vol. 116, p. 195-221.
Nunan, Journal of Catalysis, 1989, vol. 116, p. 222-229.
Olson, Energy and Environmental Research Center: Semi-Annal Report Jan. 1-Jun. 30, 1996.
Perez-Ramirez, Chemistry: A European Journal, 2007, vol. 13, 870-878.
Sathish, Chemistry of Materials, 2007, vol. 19 p. 2398-2400.
Sels, Catalysis Reviews: Science and Engineering, 2001, vol. 43, Issue 4, p. 444-488.
Shen, The Journal of Physical Chemistry C, 2008, vol. 112, p. 13114-13120.
Songhai, The Journal of Physical Chemistry B, 2004, vol. 108, p. 11561-11566.
Sreenath, Bioresource Technology, 2000, vol. 72, 253-260.
Surisetty, Applied Catalysis A: General, 2009, vol. 365, Issue 2, p. 243-251.
Surisetty, Applied Catalysis A: General, 2010, vol. 381, Issue 1-2, p. 282-288.
Tien-Thao, Applied Catalysis A: General, 2006, vol. 311, p. 204-212.
Tien-Thao, Journal of Catalysis, 2007, vol. 245, Issue 2, p. 348-357.
Toebes, Catalysis Today, 2002, vol. 76, p. 33-42.
Van Laar, Journal of Catalysis, 2001, vol. 197, p. 139-150.
Woo, Journal of Catalysis, 1993, vol. 192, p. 672-690.
Wu, Applied Catalysis A: General, 2008, vol. 340, Issue 1, p. 87-97.
Wu, Chemistry of Materials, 2007, vol. 19, p. 1577-1583.
Zavoianu, Applied Catalysis A: General, 2005, vol. 286, p. 211-220.
Zhang, Chemical Communications, 2010, vol. 46, 862-864.
PCT/US2011/062757, International Preliminary Report on Patentability.
PCT/US2011/062757, International Search Report and Written Opinion of the International Searching Authority.
PCT/US2011/062757, Response to Search Report and Written Opinion.
PCT/US2011/062757, Response to Second Written Opinion.
PCT/US2011/062757, Written Opinion of the International Preliminary Examining Authority.
PCT/US2011/062760 International Search Report and Written Opinion of the International Searching Authority.
PCT/US2011/062760, International Preliminary Report on Patentability.
PCT/US2011/062760 second Written Opinion of the International Searching Authority.
PCT/US2011/062760 Response to Second Written Opinion.
PCT/US2011/062760, Response to Search Report and Written Opinion.
Chinese Office Action dated Jul. 11, 2016 pertaining to Chinese Application No. 201180066949.6.
Olson et al., "Task 4.9—Value-Added Products from Syngas", DOE/MC/30097—5589, Semi-Annual Report Jul. 1-Dec. 31, 1996.

1

CATALYST COMPOSITIONS FOR CONVERTING SYNGAS TO PRODUCE HIGHER ALCOHOLS

This application is a non-provisional application claiming priority from the U.S. Provisional Patent Application No. 61/419,941, filed on Dec. 6, 2010, entitled "CATALYST COMPOSITIONS FOR CONVERTING SYNGAS TO PRODUCE HIGHER ALCOHOLS," the teachings of which are incorporated by reference herein as if reproduced in full hereinbelow.

BACKGROUND

Field of the Invention

The present invention relates to synthesis of ethanol and other higher alcohols from syngas. More particularly, it relates to supported molybdenum-containing catalyst compositions for accomplishing this synthesis.

Background of the Art

Alcohols, particularly those ranging from methanol to hexanol (C1-6OH), are important products that can be synthesized from synthesis gas. Synthesis gas ("syngas") is a mixture of hydrogen gas and carbon monoxide gas ($H_2$/CO). The produced alcohols are useful both as fuels and as chemicals for a variety of manufacturing processes. Among these, those defined herein as higher alcohols, i.e., alcohols having at least two carbon atoms ($C2^+$), are currently sought to serve as, for example, automobile fuels and fuel blends. In these applications they may offer desirably high octane number along with desirably low emissions of nitrogen oxide ($NO_x$), ozone, CO, and aromatic vapors. In addition, the higher alcohols may be useful as alternative feedstocks for important olefins (produced via dehydration of the alcohol), particularly when the syngas is derived from biomass or coal.

Useful higher alcohols may be directly and catalytically synthesized from syngas. Researchers have identified three general types of catalysts that are capable of carrying out this synthesis. These types include: (i) mixed metal oxides promoted with alkali metals, which are known as "modified methanol synthesis catalysts;" (ii) alkali-doped molybdenum sulfide catalysts; and (iii) noble and/or transition metal catalysts on oxide supports. Although such catalysts are often used with the intention of producing higher alcohols in particular, each of these three catalyst types tends to show preferential selectivity toward methanol ($CH_3OH$, alternatively "MeOH") and/or methane ($CH_4$). Thus, yields of the higher alcohols in such processes are often poor.

Because of this preferential selectivity, much research has been devoted to improving the yield of the higher alcohols, particularly ethanol, propanol, and butanol ($C_2H_5OH$, alternatively "EtOH"; $C_3H_7OH$; and $C_4H_9OH$, respectively; i.e., C2-4OH). U.S. Pat. Nos. 4,590,314 and 4,609,678 disclose processes for making an alcohol mixture, preferably containing no more than 85 weight percent (wt %) methanol, wherein catalysts of copper/thorium/alkali metal oxides are used. U.S. Pat. Nos. 4,607,055 and 4,661,525 disclose catalysts consisting of molybdenum (Mo) and cobalt (Co), iron (Fe), or nickel (Ni), promoted by an alkali metal. In another example the catalyst is an alkali metal-promoted cobalt/molybdenum sulfide ($Co/MoS_2$) that has been mixed with a clay or impregnated with nanotubes. U.S. Pat. No. 4,675,344 teaches using Mo or tungsten (W) catalysts to convert a syngas feed including hydrogen sulfide ($H_2S$). However, where fewer than 57 parts per million by volume (ppmv) of $H_2S$ is included in the feed and a potassium carbonate/cobalt/molybdenum sulfide/carbon ($K_2CO_3$/Co/$MoS_2$/C) catalyst is used, MeOH is the dominant product.

U.S. Pat. No. 7,449,425 discloses use of an ionic clay-supported rhenium/manganese (Re/Mn) catalyst. The product selectivity to MeOH is 65.4 wt %; EtOH is 4.8 wt %; dimethyl ether (DME) is 6.1 wt %; and methane is 19.9 wt %, respectively, when the catalyst is a combination of 3 wt % Re and 3 wt % hydrated manganese/magnesium aluminum dihydroxide carbonate ($Mn/Mg_{0.34}Al_{0.66}(OH)_2(CO_3)_{0.33} \cdot mH_2O$), where m is the number of moles of the water of hydration and is an integer ranging from 0 to 2. U.S. Pat. No. 7,314,960 discloses the catalytic synthesis of an oxygenate from an alcohol over a copper/zinc/magnesium/aluminum (Cu/Zn/Mg/Al) based catalyst. U.S. Pat. Nos. 7,700,810; 7,700,811; 7,700,813; and 7,705,192 disclose conversion of C1-2 alcohols (MeOH and EtOH) to 1-butanol and isobutanol on a thermally decomposed Cu/Zn/Mg/Al hydrotalcite catalyst. U.S. Pat. No. 7,718,832 discloses a combination catalytic process for producing EtOH from syngas using a series of three different catalyst beds within a single reactor. The first stage is the hydrogenation of CO to form MeOH, and the other beds serve to promote both the homologation of MeOH with $H_2$ and CO to form EtOH, and the hydrogenation of other oxygenates to form higher alcohols.

Despite the many efforts to identify catalysts enabling improved selectivity to higher alcohols ($C2^+OH$), there remains a need for even greater selectivity enhancement. Greater control of selectivity, combined with the low cost and high availability of syngas, offers the possibility of lower cost and more convenient manufacture of a wide variety of products based on alcohols.

SUMMARY OF THE INVENTION

In one embodiment the invention provides a catalyst composition comprising molybdenum and an alkali metal impregnated on a hydrotalcite or hydrotalcite-like support.

In another embodiment the invention provides a process for preparing a catalyst composition comprising impregnating a hydrotalcite or hydrotalcite-like support with a source of molybdenum and a source of an alkali metal.

In yet another embodiment the invention provides a process for preparing higher alcohols comprising contacting, under conditions suitable to form a product including at least one higher alcohol, a gas mixture, including at least hydrogen gas and carbon monoxide gas, and a catalyst composition including a hydrotalcite or hydrotalcite-like support impregnated with molybdenum and an alkali metal.

DETAILED DESCRIPTION OF THE EMBODIMENTS

A key aspect of the invention is a family of novel catalyst compositions that may be prepared and used to convert syngas into a product exhibiting a selectivity toward higher ($C2^+$) alcohols that is enhanced relative to the selectivity toward higher alcohols of many other known syngas-to-alcohol conversion catalysts. The catalyst compositions comprise a combination of catalytically active metal components on a basic support that is derived from a layered double hydroxide precursor.

The basic support is derived from a layered double hydroxide of magnesium (Mg) and aluminum (Al) known as hydrotalcite. Hydrotalcite is available in both natural and synthetic form. Natural hydrotalcite is a hydrated magnesium, aluminum and carbonate-containing composition having a composition that is represented as:

(Formula 1)

$$Mg_6Al_2(OH)_{16}(CO_3)\cdot 4H_2O. \quad (1)$$

Various synthetic "hydrotalcites" may include those of identical composition with natural hydrotalcite, but may further include "hydrotalcites" that are defined herein as "hydrotalcite-like compounds." These "hydrotalcite-like compounds" have compositions wherein the carbonate anion ($CO_3^{2-}$) has been replaced with another anion. Such other anion may be selected from, in non-limiting example, phosphate ($PO_4^{3-}$), molybdate ($MoO_4^{2-}$), sulfate ($SO_4^{2-}$), nitrate ($NO_3^-$), chlorate ($ClO_3^-$), chloride ($Cl^-$), bromide ($Br^-$), fluoride ($F^-$), iodide ($I^-$) and combinations thereof. Such "hydrotalcite-like compounds" may also differ from natural hydrotalcite in comprising differing types and proportions of the divalent and trivalent metal ions, i.e., the $Mg^{2+}$ and $Al^{3+}$. For example, the $Mg^{2+}$ may be replaced, in whole or in part, by nickel ($N^{2+}$) and/or cobalt ($Co^{2+}$), and/or the $Al^{3+}$ may be replaced by cobalt ($Co^{3+}$). In fact, selection of appropriate types and proportions of these may enable those skilled in the art to ensure that the catalyst support exhibits at least some degree of basicity, as discussed further hereinbelow. In view of these variations, it may be stated that the hydrotalcite and hydrotalcite-like compounds useful in the invention, including but not limited to natural hydrotalcite as defined hereinabove, may be described by the formula:

(Formula 2)

$$M^{2+}_{1-x}M^{3+}_x(OH)_2(CO_3)_{x/2}\cdot mH_2O, \quad (2)$$

wherein $M^{2+}$ is a divalent metal selected from magnesium, cobalt and nickel; $M^{3+}$ is a trivalent metal selected from aluminum and cobalt, provided that $M^{3+}$ is not the same element as $M^{2+}$; x is the number of moles of the trivalent metal; and m is the number of moles of waters of hydration.

The catalyst support may be prepared by any effective method known to those skilled in the art. One particularly convenient method is co-precipitation. In general this involves initially dissolving a compound of each of the desired metals, e.g., magnesium and aluminum, in a solvent. The solvent may be, for example, water or a mineral acid, and is preferably, for the sake of convenience, water. Accordingly, an aqueous first salt solution may be prepared, containing the selected divalent and trivalent metals in a molar ratio of divalent metal to trivalent metal ranging from 0.5:1 to 9:1, more desirably 1:4 to 4:1. This salt may include as its anion a nitrate, acetate, sulfate, perchlorate, or chloride anion, or a combination thereof, but nitrates are, in one particular embodiment, preferred. This first salt solution is added to or combined with a second salt solution, which is also desirably aqueous. The second salt solution contains an alkali metal-containing salt, wherein the alkali metal is selected from potassium (K), sodium (Na), cesium (Cs), lithium (Li), and rubidium (Rb); an ammonium ($NH_4^+$) salt; or a combination thereof. The anion of the salt in this second solution may be, for example, carbonate, bicarbonate, phosphate, hydroxide, or a combination thereof. Thus, non-limiting examples of the salt used in the second salt solution may include potassium carbonate ($K_2CO_3$) and sodium bicarbonate ($NaHCO_3$), and in one particular embodiment, $K_2CO_3$ is conveniently employed. The two salt solutions are then combined to produce a single solution.

At this point it is important to adjust the pH of the solution, generally upward, to ensure it is sufficiently basic. As defined herein, such desirable alkalinity is confirmed by a measured pH ranging from 8 to 12, preferably from 8 to 11, and most preferably from 8.5 to 10. To ensure this desirable pH range, a typical basic reagent, for example, a sodium hydroxide (NaOH) solution, potassium hydroxide, ammonium hydroxide, or a combination thereof, may be added in suitable amount.

The resulting suspension, containing water and an increasing amount of precipitate conforming to Formula 2, may then be aged. It generally takes several hours, frequently ranging from 18 to 25 hours, for the desired hydrotalcite or hydrotalcite-like precipitate to complete formation. In preferred embodiments the suspension is maintained at a temperature in excess of 50° C. during aging. For example, stirring the suspension for from 12 to 48 hours preferably 24 hours, at a temperature ranging from 50° C. to 80° C., preferably from 60° C. to 70° C., may be sufficient to optimize formation of the hydrotalcite or hydrotalcite-like precipitate.

Following aging, the precipitate may be filtered, washed with distilled water, and subsequently dried. Filtration and washing are desirably continued under the higher temperature used for aging, including use of water in the same temperature range. Drying may be conveniently carried out in an oven, where, for example, drying in air at a temperature from 75° C. to 100° C. for a period of from 4 to 24 hours, preferably from 4 to 6 hours, may be effective.

In order to ensure that the hydrotalcite or hydrotalcite-like compound conforms with Formula 2, powder X-ray diffraction (XRD) may be carried out using copper K-alpha radiation. Where angle 2-theta peaks are confirmed at d-spacings of 11.5; 23.1; 27.1; 34.3; 38.2; 45.3; 60.5; 61.9; and 64.7, a hydrotalcite phase is present. This phase is considered to be isostructural with the hydrotalcite $Mg_6Al_2(OH)_{16}(CO_3)\cdot 16H_2O$ (JCPDS card #54-1030). The dried precipitate, which generally has a Brunauer-Emmett-Teller (BET) surface area in the range of from 50 to 250 square meters per gram ($m^2/g$), may be directly used as a support for the inventive catalyst compositions.

Alternatively, the dried precipitate may be further thermally modified by calcination at a temperature ranging from 200° C. to 600° C., preferably from 300° C. to 500° C., in air, for a period of time ranging from 1 to 8 hours, preferably from 1 to 4 hours. The obtained solid may be analyzed by powder XRD as described hereinabove, in order to confirm disappearance of the hydrotalcite reflection lines and the appearance of new peaks corresponding to the mixed Mg(Al)$O_x$ oxide (JCPDS card #45-0946). These peaks correspond to d-spacings at angles 2-theta of 35.1; 43.4; and 62.5. The calcined material desirably has a BET surface area ranging from 5 to 250 $m^2/g$.

The catalyst compositions of the invention further include K and Mo components, which supply the sites for CO adsorption, CO dissociation and hydrogenation that are necessary to the catalysis process in converting syngas to alcohols. These may be incorporated onto the support in a variety of ways known to those skilled in the art. For example, the calcined hydrotalcite or hydrotalcite-like support may be impregnated with a source of Mo, which is, in some embodiments, in the form of a soluble salt. This is carried out at a temperature and pH that are suitable to ensure impregnation of the Mo, which may include a temperature ranging from 30° C. to 120° C., preferably from 50° C. to 80° C., and a pH ranging, from 3 to 10, preferably from 7 to 9. The impregnated hydrotalcite or hydrotalcite-like support may then be dried in an oven, preferably at a temperature ranging from 90° C. to 130° C., e.g., 105° C., overnight and then heated at a temperature from 300° C. to 500° C., e.g., 500° C. This heating after impregnation facilitates decomposition of components of the molybdenum source other than molybdenum, forming molybdenum oxide domains on the hydrotalcite or hydrotalcite-like support, and is not considered to be a calcination but is, rather, termed herein a thermal treatment.

Proportions of the foregoing materials may be varied according to the understanding of those skilled in the art. However, in some embodiments it may be preferred to employ a molar ratio of the molybdenum to the alkali metal ranging from 5:1 to 1:5, and more preferably from 3:1 to 1:3. In general it may be preferred that the amount of molybdenum range from 1 to 20 wt %, and more desirably from 5 to 10 wt %, based on weight of the total catalyst composition. It is also desirable that the alkali metal range from 2.5 to 20 wt %, and more preferably from 5 to 10 wt %, on the same basis. For example, in certain embodiments a molybdenum amount of 10 wt % in combination with an alkali metal amount of 10 wt % may be particularly effective.

Once the impregnated support, i.e., the inventive catalyst composition, has been formed, its character may be confirmed by means of powder XRD, transmission electron microscopy (TEM), and nitrogen ($N_2$) physisorption. Powder XRD, using copper alpha radiation, shows strong reflection lines at angle 2-theta d-spacings of 26.1; 28.0; and 36.9. These reflections correspond to a molybdenum dioxide phase, at a $MoO_2$ loading of 30 wt %, which is 22.5 wt % of Mo metal. Because XRD of the composition does not exhibit reflections that are characteristic of crystalline structure where molybdenum loadings are below 10 wt %, the existence of molybdenum structures in those cases may desirably be confirmed instead by means of Extended X-ray Absorption Fine Structure (EXAFS), X-ray Absorption Near-edge Spectroscopy (XANES), and X-ray Photoelectron Spectroscopy (XPS) analyses. For example, at a Mo loading of 5 wt %, XPS spectra show the energy binding of $Mo^{4+}$ and $S^{2-}$ at 229.1 eV ($Mo^{3d}$) and 162.1 eV ($S^{2p}$), respectively. EXFAS analysis in the same instance results in a coordinated number, at 5 wt % Mo/Mg(Al)$O_x$, of about 4.2±0.3. TEM analysis shows zones in the catalyst composition of layered oxide structure and zones where the support appears amorphous. The composition's specific surface area, determined by $N_2$ physisorption and calculated as BET surface area, is generally in the range of from 120 to 230 $m^2/g$, and in particular embodiments, from 170 to 210 $m^2/g$. The average pore diameter of the catalyst composition ranges from 15 to 35 nm. The average pore volume ranges from 0.5 to 1.1 cubic centimeters per gram ($cm^3/g$).

The inventive catalyst compositions may be used for catalytic processes according to the understanding of those skilled in the art. Potential applications may include, but are not necessarily limited to, production of higher alcohols from syngas, i.e., from a mixture of $H_2$ gas and CO gas, or via methanol homologation. A useful source of syngas is hydrocarbon feed stocks, such as oil, coal, and renewable feed stocks, including, for example, biomass. For this purpose the mole ratio of $H_2$ to CO is desirably from 0.1 to 5 moles of $H_2$ per mole of CO, preferably from 0.5 to 2 moles of $H_2$ per mole of CO. In general, the catalyst compositions may be employed in any apparatus and configuration enabling flow of the syngas combined with adequate contact between the syngas and the catalyst composition. Such may include, but is not limited to, fixed beds, moveable beds, fluidized beds, and the like.

In certain embodiments it may be desirable to pretreat the catalyst composition prior to using it for the syngas conversion, i.e., prior to contacting the catalyst and the syngas or other gas mixture including both $H_2$ and CO. Such pretreatment serves to impregnate the hydrotalcite or hydrotalcite-like support with sulfur, which is obtained from a sulfur source. This may be carried out using any means or method known to those skilled in the art, but generally involves heating the catalyst composition and exposing it to an $H_2S/H_2$ feed in order to sulfide it. For example, it may be effective for the $H_2S$ to be present in an amount of from 10 to 30 volume percent (vol %), preferably 20 vol %, in the $H_2S/H_2$ feed, and to contact the gas mixture and the Mo/alkali metal-impregnated support at a temperature ranging from 200° C. to 600° C., for example, at 450° C. Time may range from 1 to 4 hours in many embodiments, with 2 hours being often sufficient for effective sulfidation. In this case the temperature may be achieved by way of a ramping protocol, for example, ramping to 450° C. at a rate of 5° C./min, then beginning the heating period as soon as desired temperature is attained.

The character of the sulfided catalyst compositions may be confirmed by, for example, powder XRD. Reflection lines (2-theta) at 14.4; 32.2; 39.3; and 58.3; are characteristic of the $MoS_2$ phase, where the loading of Mo is 6.66 wt %. The BET surface area of the sulfided catalyst may typically range from 1 to 150 $m^2/g$, and in particular embodiments, from 1 to 120 $m^2/g$.

In an alternative embodiment it is also possible to use the catalyst compositions without prior sulfidation for the production of higher alcohols from syngas. In this embodiment the catalyst compositions may be pretreated by exposure to an argon (Ar) or other inert gas feed for 1 hour at a rate of 50 mL/min. $N_2$ gas is less preferred because, though inert, it may leave a slight residue that can interfere with use of $N_2$ as an internal standard. An amount of $H_2S$, for example, 50 ppm, may then be incorporated in the syngas feed. The result is that the catalyst is slowly sulfided in situ. In this embodiment the catalyst compositions may attain their maximum activity only after significant sulfidation has been accomplished.

Reaction conditions for effective the conversion of the syngas feed to higher alcohols (often in combination with some methanol) may include a reaction temperature ranging from 235° C. to 360° C.; a pressure ranging from 500 psig to 3,000 psig (3.45 to 20.68 MPa), preferably from 1,000 psig to 2,500 psig (6.89 to 17.24 MPa); and a GHSV ranging from 600 mL/g/h to 2,400 mL/g/h. Generally it is preferred that the feed include at least two constituents: Syngas, in a mole ratio of $H_2$ to CO of 1 and an amount from 99 to 85 vol %; and a small concentration (from 20 to 250 ppm) of $H_2S$. A proportion of $N_2$ ranging from 1 to 15 vol % may be tolerated, although it is preferably absent from the feed. Even if the catalyst composition has been presulfided, the small amount of $H_2S$ enhances its stability. $N_2$ may then be used as an internal standard upon which the CO conversion and overall mass balance of the reaction may be calculated.

In general the conversion of CO may range from 2 to 30 mol %, although the process may be carried out to accomplish a greater or lesser conversion. Selectivity to $C2^+OH$ products may, in particular embodiments, range from 40 to 75 carbon atom mol %, while the selectivity to methanol may range from 1 to 20 carbon atom mol %, as calculated excluding $CO_2$. In many embodiments the primary products are ethanol and n-propanol, while selectivity to methane, a major hydrocarbon product, may range from 10 to 40 mol %.

EXAMPLES

Example 1

Preparation of Support #1

First, an amount of 1.60 g of sodium carbonate is dissolved in 25 mL of water in a 500 mL beaker. The solution is heated to 65° C. Then, a quantity of 11.25 g of aluminum nitrate nonahydrate ($Al(NO_3)_3 \cdot 9H_2O$, 99+%) and 17.92 g of magnesium nitrate hexahydrate ($Mg(NO_3)_2 \cdot 6H_2O$, 99+%) are dissolved in 150 mL of deionized (DI) water. The resulting suspension is added drop-wise to the preheated $Na_2CO_3$ solution. The pH of the solution is adjusted to approximately 9.50 using 1.5 molar (M) sodium hydroxide (MOH) solution.

After completing addition of the metal nitrate solutions, the resulting suspension is kept at 65° C. with stirring for 24 h. The precipitate is separated from the solution by filtering and washed with 1000 mL of hot DI water. The filter cake is dried in an oven at 105° C. overnight and calcined at 450° C. for 2 hours in air to obtain Support #1.

BET surface area of the uncalcined Support #1 is about 142 $m^2/g$. XRD of the uncalcined hydrotalcite support, 2-theta: 11.5; 23.1; 27.1; 34.4; 38.2; 45.3; 60.5; 61.9; 64.7. XRD of the calcined support, 2-theta: 43.2; and 62.6.

Example 2

Preparation of Support #2

First, an amount of 2.50 g of sodium carbonate is dissolved in 25 mL of water in a 500 mL beaker. The solution is heated to 65° C. Then, a quantity of 18.76 g of aluminum nitrate nonahydrate ($Al(NO_3)_3 \cdot 9H_2O$, 99+%) and 12.82 g of magnesium nitrate hexahydrate ($Mg(NO_3)_2 \cdot 6H_2O$, 99+%) are dissolved in 150 mL of DI water. The resulting suspension solution is added drop-wise to the preheated $Na_2CO_3$ solution. The pH of the solution is adjusted to approximately 9.50 using 1.5 M sodium hydroxide solution.

After complete addition of the metal nitrate solutions, the resulting suspension is kept at 65° C. with stirring for 24 h. The precipitate is separated from solution by filtering, washed with 1000 mL of hot DI water. The filter cake is dried in an oven at 105° C. overnight and calcined at 450° C. for 2 h in air to obtain Support #2.

BET surface area of the uncalcined Support #2 is about 80 $m^2/g$. XRD of the uncalcined hydrotalcite support, 2-theta: 11.7; 18.4; 20.2; 23.3; 27.1; 34.7; 39.2; 39.4 45.3; 60.7; 62.1. XRD of the calcined support, 2-theta: 43.2; 62.6.

Example 3

Preparation of Catalyst Composition A

First, 5.34 g of Support #1 described in Example 1 and 0.73 g of ammonium heptamolybdate ($(NH_4)_6Mo_7O_{24} \cdot 4H_2O$) are added in 10 g of isopropanol. The resulting suspension is stirred at 65° C. for 2 h before evaporation in an oven at 105° C. overnight. The resultant solid is calcined in a ½ inch diameter quartz tube at 500° C. for 2 h at a ramp of 5° C./min in a flow of 50 mL/min of $N_2$. The calcined solid is then added into 10 g of DI water containing 0.28 g of $K_2CO_3$ at room temperature. The slurry is dried in an oven at 105° C. overnight. The dried solid is calcined in the quartz tube at 400° C. for an hour at a ramp of 5° C./min in flow of 50 mL/min of $N_2$. The molybdenum loading calculated as molybdenum trioxide is about 10 wt %, and the $K_2CO_3$ loading is about 5 wt %.

BET surface area of the calcined catalyst composition is 69 $m^2/g$. XRD: $Mg(Al)O_x$ oxide (2-theta): 43.4; 62.6.

Example 4

Preparation of Catalyst Composition B

First, 5.67 g of Support #1 described in Example 1 and 1.74 g of ammonium heptamolybdate ($(NH_4)_6Mo_7O_{24} \cdot 4H_2O$) are added in 11.5 g of isopropanol. The resulting suspension is stirred at 65° C. for 2 hours before evaporation in an oven at 105° C. overnight. The resultant solid is calcined in a ½ inch diameter quartz tube at 500° C. for 2 h at a ramp of 5° C./min in flow of 50 mL/min of $N_2$. The calcined solid is then added into 11.5 g of DI water containing 0.68 g of $K_2CO_3$ at room temperature. The slurry is dried in an oven at 105° C. overnight. The dried solid is calcined in the quartz tube at 400° C. for an hour at a ramp of 5° C./min in a flow of 50 mL/min of $N_2$. The molybdenum loading calculated as molybdenum trioxide is about 20 wt %, and the $K_2CO_3$ loading is about 10 wt %.

The BET surface area of the catalyst composition is from 9 to 47 $m^2/g$. XRD: $K_2Mo_2O_7$ (2-theta): 18.8; 29.3; 30.6; $K_2Mo_4O_6$ (2-theta): 25.5; 39.7; $MoO_2$ (2-theta): 26.2; 28.1; $Mg(Al)O_x$ oxide (2 theta): 43.1; 62.4.

Example 5

Preparation of Catalyst Composition C

First, 4.58 g of Support #1 described in Example 1 and 2.4 g of ammonium heptamolybdate ($(NH_4)_6Mo_7O_{24} \cdot 4H_2O$) are added in 9.0 g of isopropanol. The resulting suspension is stirred at 65° C. for 2 h before evaporation in an oven at 105° C. overnight. The resultant solid is calcined in a ½ inch diameter quartz tube at 500° C. for 2 h at a ramp of 5° C./min in flow of 50 mL/min of $N_2$. The calcined solid is then added into 9.0 g of DI water containing 0.94 g of $K_2CO_3$ at room temperature. The slurry is dried in an oven at 105° C. overnight. The dried solid is calcined in the quartz tube at 400° C. for an hour at a ramp of 5° C./min in flow of 50 mL/min of $N_2$. The molybdenum loading calculated as molybdenum trioxide is about 30 wt %, and the $K_2CO_3$ loading is about 15 wt %.

BET surface area of the catalyst composition is about 14 to 18 $m^2/g$. XRD: $MoO_2$ (2-theta): 26.1; 37.0; $Mg(Al)O_x$ oxide (2-theta): 43.2; 62.6.

Example 6

Preparation of Catalyst Composition D

First, an amount of 4.58 g of Support #1 described in Example 1 and 0.62 g of ammonium heptamolybdate ($(NH_4)_6Mo_7O_{24} \cdot 4H_2O$) are added in 9.0 g of isopropanol. The resulting suspension is stirred at 65° C. for 2 hours before evaporation in an oven at 105° C. overnight. The resultant solid is calcined in the ½ inch quartz tube at 500° C. for 2 h at a ramp of 5° C./min in flow of 50 mL/min of $N_2$. The calcined solid is then added into 9.0 g of DI water containing 0.74 g of $K_2CO_3$ at room temperature. The slurry is evaporated and dried in an oven at 105° C. overnight. The dried solid is calcined in the quartz tube at 400° C. for an hour at a ramp of 5° C./min in flow of 50 mL/min of $N_2$. The molybdenum loading calculated as molybdenum trioxide is about 10 wt %, and the $K_2CO_3$ loading is about 15 wt %.

BET surface area of the catalyst is about 47 m²/g. XRD: $K_2Mo_2O_7$ (2-theta): 18.9; 23.3; 29.3; 30.6; $K_2Mo_4O_6$ (2-theta): 26.3, 39.7; $Mg(Al)O_x$ oxide (2-theta): 43.2; 62.7.

Example 7

Preparation of Catalyst Composition E

First, 4.76 g of Support #2 described in Example 2 and 2.51 g of ammonium heptamolybdate (($NH_4)_6Mo_7O_{24} \cdot 4H_2O$) are added in 9.0 g of isopropanol. The resulting suspension is kept at 65° C. with stirring for 2 h before evaporation in an oven at 105° C. overnight. The resultant solid is calcined in a ½ inch diameter quartz tube at 500° C. for 2 h at a ramp of 5° C./min in flow of 50 mL/min of $N_2$. The calcined solid is then added into 9.0 g of DI water containing 0.98 g of $K_2CO_3$ at room temperature. The slurry is dried in an oven at 105° C. overnight. The dried solid is calcined in the quartz tube at 400° C. for an hour at a ramp of 5° C./min in flow of 50 mL/min of $N_2$. The molybdenum loading calculated as molybdenum trioxide is about 30 wt %, and the $K_2CO_3$ loading is about 15 wt %.

The BET surface area of the catalyst is about 8.0 m²/g. XRD: $MoO_2$ (2-theta): 26.1; 36.7; $Mg(Al)O_x$ oxide (2-theta) 43.6; 62.7.

Example 8

Preparation of Catalyst F

First, 3.71 g of Support #2 described in Example 2 and 0.51 g of ammonium heptamolybdate (($NH_4)_6Mo_7O_{24} \cdot 4O_2O$) are added in 7.0 g of isopropanol. The resulting suspension is kept at 65° C. with stirring for 2 hours before evaporation in an oven at 105° C. overnight. The resultant solid is calcined in a ½ inch diameter quartz tube at 500° C. for 2 hours at a ramp of 5° C./min in a flow of 50 mL/min of $N_2$. The calcined solid is then added into 7.0 g of DI water containing 0.19 g of $K_2CO_3$ at room temperature. The slurry is dried in oven at 105° C. overnight. The dried solid is calcined in the quartz tube at 400° C. for an hour at a ramp of 5° C./min in a flow of 50 mL/min of $N_2$. The molybdenum loading calculated as molybdenum trioxide is about 10 wt %, and the $K_2CO_3$ loading is about 5 wt %.

The BET surface area of the catalyst is about 77 m²/g. XRD, $Mg(Al)O_x$ oxide (2-theta): 43.1; 62.8.

Example 9

Preparation of Catalyst G

First, 1.027 g of ammonium heptamolybdate (($NH_4)_6Mo_7O_{24} \cdot 4H_2O$) is added to 28.8 g dimethyl sulfoxide and stirred for 4 hours at 23° C. The solution is then added to a beaker containing 7.59 g of support similar to that described in Example 2 and heated to 135° C. for 12 hours in air. The resultant solid is calcined in a ½ inch diameter quartz tube first at 200° C. for 4 hours at a ramp of 5° C./min in a flow of 50 mL/min of $N_2$ and then at 450° C. for 2 hours at a ramp of 5° C./min in a flow of 50 mL/min of $N_2$. Finally, the calcined solid is combined with 0.42 g $K_2CO_3$ and ground in a mortar and pestle at 23° C. for 15 minutes. The molybdenum loading calculated as molybdenum trioxide is about 10 wt %, and the $K_2CO_3$ loading is about 5 wt %.

The BET surface area of the catalyst is about 143 m²/g. XRD, $Mg(Al)O_x$ oxide (2-theta): 43.4; 62.6.

Example 10

Preparation of Higher Alcohols

A series of tests of the six catalyst compositions, designated as Catalyst Compositions A-F as shown in Examples 3-8, is carried out to measure their performance in converting syngas into higher alcohols. The reactor used consists of a quarter-inch stainless steel (SS) tube (316 SS) with a catalyst loading of 1.0 g. Premixed hydrogen, carbon monoxide, and nitrogen feed gases from cylinders are compressed and regulated at the reaction pressure stated in the following tables. The feed gas mixture contains hydrogen and carbon monoxide at the molar ratio of 1/1 with about 10 percent by volume nitrogen, serving as an internal standard. About 50 ppm of $H_2S$ is also present in the feed gas.

The mixed feed gas passes through a bed of molecular sieve 13× held at 170° C. to remove iron carbonyl and any other carbonyl contaminants that may be present. The feed gas then passes, at a pre-determined gas hourly space velocity (GHSV) of 1200, 1750, or 2400 milliliters per gram per hour (mL/g/h), through the fixed bed reactor that is kept at the stated reaction temperature and held at a pressure of 1,500 pounds per square inch gauge (psig) (10.34 megapascals, MPa). The reactor effluent is fed into a gas chromatograph to analyze the gas composition, and the catalytic performance of the solids is summarized in Tables 1-3 hereinbelow. "Selectivity," in carbon mole percent, excluding $CO_2$, is defined as the carbon atom content in each product divided by the sum of carbon atoms in all alcohols, non-alcohol oxygenates, and hydrocarbons. "Hydrocarbons" are primarily methane, and "Oxygenates" are the total of oxygen-containing products other than alcohols.

Table 1 shows performance of Catalyst Compositions A-E, with results recorded under the following relevant conditions: Temperature=310° C.; $H_2/CO$=1; $H_2S$ (ppm)=50; catalyst weight=1.0 g; and GHSV=1200 mL/g/h.

TABLE 1

| Catalyst | CO Conversion (%) | $CO_2$ (%) | Selectivity (C, %, Excluding $CO_2$) | | | |
|---|---|---|---|---|---|---|
| | | | MeOH | $C_2^+OH$ | Oxygenates | Hydrocarbons |
| A | 9.9 | 35.1 | 3.3 | 65.5 | 4.1 | 27.1 |
| B | 7.5 | 31.1 | 4.4 | 49.4 | 3.6 | 42.5 |
| C | 12.0 | 23.9 | 8.1 | 42.2 | 1.5 | 59.5 |
| D | 5.8 | 27.6 | 8.9 | 44.3 | 2.4 | 44.5 |
| E | 13.7 | 29.9 | 4.8 | 44.0 | 2.3 | 49.3 |

Table 2 shows results for the same catalysts, based upon a GHSV of 2400 mL/g/h. All other conditions are the same as those for Table 1.

TABLE 2

| Catalyst | CO Conversion (%) | $CO_2$ (%) | Selectivity (C, %, Excluding $CO_2$) | | | |
|---|---|---|---|---|---|---|
| | | | MeOH | $C_2^+OH$ | Oxygenates | Hydrocarbons |
| A | 7.2 | 31.4 | 6.1 | 60.5 | 2.3 | 31.6 |
| B | 2.6 | 30.5 | 12.5 | 44.0 | 7.3 | 36.1 |
| C | 4.1 | 24.3 | 13.1 | 37.4 | 2.4 | 46.8 |
| D | 2.9 | 28.7 | 13.9 | 51.1 | 5.6 | 29.4 |
| E | 6.8 | 28.9 | 8.5 | 43.6 | 3.8 | 44.0 |

Table 3 shows results for only Catalyst Composition F (Example 8), at temperatures ranging from 260° C. to 335°

C. Test conditions include H$_2$/CO=1; GHSV (mL/g/h)=1750; H$_2$S (ppm)=50; and weight of catalyst (g)=0.7.

TABLE 3

| Temperature, °C. | CO Conversion (%) | CO$_2$ (%) | Selectivity (C, %, Excluding CO$_2$) | | | |
|---|---|---|---|---|---|---|
| | | | MeOH | C2$^+$OH | Oxygenates | Hydrocarbons |
| 260 | 1.9 | 43.0 | 3.9 | 72.6 | 4.9 | 18.5 |
| 285 | 3.2 | 46.3 | 3.8 | 76.6 | 4.4 | 15.5 |
| 310 | 7.8 | 47.9 | 2.3 | 56.5 | 1.2 | 40.0 |
| 335 | 12.3 | 44.4 | 1.9 | 29.9 | 1.3 | 66.9 |

The inventive catalysts (Catalyst Compositions A-F, Examples 3-8) are useful as "low-methanol" catalysts for the conversion of syngas to non-methanol oxygenate products. In particular, the selectivity to C2$^+$OH is much higher than to methanol, by a factor ranging from 8 to 15. At a lower loading of MoO$_2$ precursor (Example 3) and a higher ratio of atomic K to Mo (Example 8), the catalysts show an improved C2$^+$OH selectivity under typical higher alcohol synthesis conditions. A highest selectivity toward C2$^+$OH from syngas is seen, in Table 3, at estimated reaction temperatures ranging from approximately 270° C. to 300° C., i.e., at 260° C. C2$^+$OH is at 72.6%; at 285° C. it increases to 76.6%; and at 310° C. it has dropped to 56.5%.

What is claimed is:

1. A catalyst composition prepared by a process comprising
   (a) calcining a hydrotalcite or hydrotalcite-like support by heating it at a temperature ranging from 200° C. to 600° C., under conditions suitable to form a calcined support exhibiting a powder X-ray diffraction pattern obtained using copper K-alpha radiation having d-spacings at angles 2-theta of 43.4, 62.5 and, optionally, 35.1; and
   (b) impregnating the calcined support with a molybdenum source and an alkali metal source, under conditions suitable to form a catalyst composition.

2. The catalyst composition of claim 1 wherein at least a portion of the molybdenum source is in the form of molybdenum sulfide.

3. The catalyst composition of claim 2 wherein the catalyst composition comprises
   from 5 weight percent to 20 weight percent of molybdenum sulfide, and
   from 2.5 weight percent to 2 weight percent of alkali metal from the alkali metal source;
   both based on the weight of the catalyst composition as a whole.

4. The catalyst composition of claim 1 wherein step (b) occurs under at least one condition selected from
   a temperature ranging from 30° C. to 120° C.,
   a time ranging from 1 hour to 4 hours, and
   combinations thereof.

5. The catalyst composition of claim 1 wherein the hydrotalcite or hydrotalcite-like support is prepared by co-precipitation of salt solutions containing divalent magnesium, nickel or cobalt ions and trivalent aluminum or cobalt ions, provided the divalent and trivalent ions represent different elements; alkali metal ions; and at least one carbonate anion; to form a product having the formula:

$$M^{2+}_{1-x}M^{3+}_x(OH)_2(CO_3)_{x/2} \cdot mH_2O,$$

wherein M$^{2+}$ is a divalent magnesium, nickel or cobalt ion, and M$^{3+}$ is a trivalent aluminum or cobalt ion, provided M$^{2+}$ and M$^{3+}$ represent different elements; x is the number of moles of the trivalent aluminum or nickel ion; m is the number of moles of waters of hydration; and wherein the carbonate anion may optionally be replaced, in whole or part, by an anion selected from the group consisting of phosphate, molydate, sulfate, nitrate, chlorate, chloride, bromide, fluoride, iodide, and combinations thereof.

6. A process for preparing a higher alcohol comprising contacting
   (a) a catalyst composition prepared by a process comprising
      (a) calcining a hydrotalcite or hydrotalcite-like support by heating it at a temperature ranging from 200° C. to 600° C., under conditions suitable to form a calcined support exhibiting a powder X-ray diffraction pattern obtained using copper K-alpha radiation having d-spacings at angles 2-theta of 43.4, 62.5 and, optionally, 35.1; and
      (b) impregnating the calcined support with a molybdenum source and an alkali metal source;
      under conditions suitable to form a catalyst composition; and
   (b) a gas mixture, including at least hydrogen gas and carbon monoxide gas;
   under conditions suitable to form a product comprising at least one higher alcohol.

7. The process of claim 6 wherein the gas mixture is part of a feed that further comprises hydrogen sulfide in an amount ranging from 20 ppm to 250 ppm.

* * * * *